(12) United States Patent
Xie et al.

(10) Patent No.: US 11,555,193 B1
(45) Date of Patent: Jan. 17, 2023

(54) GENE ANSB KNOCKOUT MUTANT OF CITROBACTER WERKMANII AND APPLICATION THEREOF

(71) Applicant: INSTITUTE OF MICROBIOLOGY, GUANGDONG ACADEMY OF SCIENCES (GUANGDONG DETECTION CENTER OF MICROBIOLOGY), Guangzhou (CN)

(72) Inventors: Xiaobao Xie, Guangzhou (CN); Gang Zhou, Guangzhou (CN); Qingshan Shi, Guangzhou (CN); Yingsi Wang, Guangzhou (CN); Hong Peng, Guangzhou (CN); Sujuan Li, Guangzhou (CN)

(73) Assignee: INSTITUTE OF MICROBIOLOGY, GUANGDONG ACADEMY OF SCIENCES (GUANGDONG DETECTION CENTER OF MICR, Guangzhou (CN)

(*) Notice: Subject to any disclaimer, the term of this patent is extended or adjusted under 35 U.S.C. 154(b) by 0 days.

(21) Appl. No.: 17/700,548

(22) Filed: Mar. 22, 2022

(30) Foreign Application Priority Data

Sep. 28, 2021 (CN) .......................... 202111141159.1

(51) Int. Cl.
| | |
|---|---|
| *C12N 15/74* | (2006.01) |
| *C07K 14/24* | (2006.01) |
| *C12N 9/80* | (2006.01) |
| *C02F 101/20* | (2006.01) |

(52) U.S. Cl.
CPC .............. *C12N 15/74* (2013.01); *C07K 14/24* (2013.01); *C12N 9/80* (2013.01); *C02F 2101/20* (2013.01); *C12Y 305/01038* (2013.01)

(58) Field of Classification Search
None
See application file for complete search history.

(56) References Cited

FOREIGN PATENT DOCUMENTS

| CN | 104789508 A | 7/2015 |
| CN | 108795832 A | 11/2018 |
| CN | 111607607 A | 9/2020 |
| KR | 102269634 B1 | 6/2021 |

OTHER PUBLICATIONS

Gang Zhou, et al., Roles of ompA of Citrobacter werkmanii in bacterial growth, biocide resistance, biofilm formation and swimming motility, Applied Microbiology and Biotechnology, 2021, pp. 2841-2854, vol. 105.
Gang Zhou, et al., Complete genome sequence of Citrobacter werkmanii strain BF-6 isolated from industrial putrefaction, BMC Genomics, 2017, pp. 1-11, vol. 18, No. 765.
Li Long-Jie, et al., Identification and biofilm formation characterization of Citrobacter werkmanii isolated from Industrial spoilage, Institute of Microbiology, CAS, 2014, pp. 2-7, vol. 41, No. 1.

*Primary Examiner* — Anand U Desai
(74) *Attorney, Agent, or Firm* — Bayramoglu Law Offices LLC (57) ABSTRACT

A gene ansB knockout mutant of *Citrobacter werkmanii* and an application thereof are provided. The gene ansB knockout mutant of the *C. werkmanii* is *C. werkmanii* with a gene ansB knocked out and a nucleotide sequence of the gene ansB is as shown in SEQ ID NO: 1. In the present invention, the acquired engineering bacteria with the gene ansB of the *C. werkmanii* knocked out are cultured in LB, TSB, NB and other media at 25° C. and 30° C., so that a biofilm formation capacity of the *C. werkmanii* on a polypropylene material is improved. Thus, the application scenarios and scopes of the *C. werkmanii* in heavy metal ion adsorption and construction of cellular protein synthesis micro-factories are broadened.

4 Claims, 4 Drawing Sheets

Specification includes a Sequence Listing.

SEQUENCE LISTING

```
<160> NUMBER OF SEQ ID NOS: 11

<210> SEQ ID NO 1
<211> LENGTH: 1047
<212> TYPE: DNA
<213> ORGANISM: Artificial Sequence
<220> FEATURE:
<223> OTHER INFORMATION: Citrobacter werkmanii GDFMZ BF-8

<400> SEQUENCE: 1
```

```
atggagttttt tcaagaaaac ggcacttgcc gcactggtta tgggtttcag cggcgcggcg      60
cttgcactgc caaacatcac tattttagca accggcggga ccattgccgg cggtggtgat     120
tccgcgacaa atctaacta cacggcaggc aaggtaggcg tagagaatct ggttgaagcc      180
gtacctcagt tgaaagacat cgcggttgtt aaaggcgagc aggtggtgaa catcggctct     240
caggatatga atgacgacgt ctggttaacg ctggcgaaaa agattaacac cgagtgtgat     300
aaaaccgacg ttttgtcgt gacacatggt acggatacca tggaagaaac tgcctatttc      360
ctcgacctga ccgtcaagtg caacaagccg gtagtgctgg tgggtgcaat gcgtccgtct     420
acagggatga gcgccgatgg cccgttcaac ctgtataacg cagtggtgac ggctgcagac     480
aaagcctctg ccaaccgtgg cgtgctggtg gtgatgaacg acaccgtgat ggatggtcgc     540
gacgtgacca aaaccaacac taccgatgta gccaccttca atccgttaa ctatggcccg      600
ctgggctaca tccataacgg caagattgac taccagcgta cgcctgcgcg taagcacacc     660
acgtctactc cgttcgatgt gtctaagctg accgaactgc cgaaagtggg gattgtttac     720
aactacgcta acgcctcgga tctgccagcc aaagcgctgg tcgacgcggg ttatgcgggt     780
atcgtcagtg cgggtgtagg taacggcaac ttgtataaaa cggtattcga tacgctggcc     840
actgccgcgc ataaaggtac cgtcgtggtg cgttcctccc gtgtaccaac cggctccacc     900
acgcaggatg ctgaagttga tgatgcgaaa tacggctttg tggcttcagg ttctctgaac     960
ccgcaaaaag cgcgtgttct gctgcagctt gcgctgacgc aaaccaagga tcctaagcag    1020
atccaggaaa tgtttaatca gtattaa                                        1047
```

<210> SEQ ID NO 2
<211> LENGTH: 978
<212> TYPE: DNA
<213> ORGANISM: Artificial Sequence
<220> FEATURE:
<223> OTHER INFORMATION: Upstream homologous sequence of ansB knockout vector

<400> SEQUENCE: 2

```
ttcgatattt ggtgggacta agtagcacag ggtcggcaaa tgccggcccg atttgtattg      60
agggaaagat atgatgcgca aaacgctgct ggcggcagtc ctcacgttca cggcgatggc     120
cgcacatgcc gattacaagt gcagcgtcac cccacgtgac gatgtgattt tgagcccaca     180
aacggtgcag gtaaaaggcg aaaacggcga tctggtcatt acccaggccg gtgatgtcac     240
ctttaacggt aagcagtaca acctcaacgc cgcacagcgt gagcaggcta aagattatca     300
ggcggcgttg cgtagcagcc tgccgtggat tgacgaaggt gccagagcgc gcgtagagaa     360
aggtcgcgtg gcactggaca aaatcatcgc caaagaggtc ggtgaaagca gcaacatgcg     420
tggccgctta accaagctgg atgcgcaatt gaaagcgcag atgaaccgca tcatcgaaca     480
tcgtactgat gggctgacct tccactataa ggcgattgac caggtccgcg ccgacgggca     540
gcaattagtg aatcaggcga tgggcggcat tttgcaggac agcatcaacg agatgggcgc     600
caaagctgtg ctcaaaggcg gtggtaaccc gctgcagggc gtgctcggga gcctcggtgg     660
tttgcaaacc tcaattcaga acgaatggaa gaatcaggaa caagacttcc agcagtttgg     720
caaagatgtt tgtgcccgcg tcgtgacgct ggaaaacgat cgtaaaacgc tggttagcac     780
gctgaaataa ttttcacctc ttttaacgg cacagaaaca ttctgtgccg ttttattttg      840
tatctttctg ttttttgat atccatctct aagaatggca atttgatgga gatataaatc      900
tggttaattg gaactcgtca cattattcat ctgtaagata gacataatgc tgcaaattca     960
```
agtaactgga gaaataac                                                 978

<210> SEQ ID NO 3
<211> LENGTH: 795
<212> TYPE: DNA
<213> ORGANISM: Artificial Sequence
<220> FEATURE:
<223> OTHER INFORMATION: Downstream sequence of ansB knockout vector

<400> SEQUENCE: 3

| | | | | |
|---|---|---|---|---|
| tcgatgcagg | tggctgcgct | tatcgcccta | accctgtagg | cctgataagc gcagcgccat | 60 |
| caggcaattt | gccggatggc | ggctcaaggt | cttatccggc | ctacatcgtt accgtattac | 120 |
| tccgccagaa | acagctccag | cagcgaattc | aaaaacagct | taccgtgttg ggtaatctgc | 180 |
| cagtattcat | cgcattcact | caggtaaccc | tgggcgatag | ctgcatcaat ctgtcgacga | 240 |
| ataacgtctt | cggcaagccc | ggtgtattgc | gtgaattctg | cacgcggcgc ggcctccagt | 300 |
| aaccggaaac | gattcataaa | gaactcgaac | ggcttgtcgg | cttcggcaac atcacgctgg | 360 |
| ctttccaggt | aacgtccttg | catgtatccg | cgtggatgcc | gcgttttggt ggtgcgcaaa | 420 |
| atgcgtccgt | ccgggaaagt | gattttgccg | tgcgcgccac | agccaatgcc aagatagtcg | 480 |
| ccaaaacgcc | agtaattgag | attgtgctga | cactgatagc | ccggcttcgc ataggctgag | 540 |
| gtttcgtact | gctgataccc | cgctgcagtc | agcaactggt | ggccttgctc aaaaatatcc | 600 |
| cacagtgcgt | catcgtccgg | tagaaccggc | ggacgtgaac | caaatagcgt gttgggttcg | 660 |
| atggtcaact | gataccagga | agatgcggc | gggttgagcg | cgatggcctg ctgcaaatca | 720 |
| ctcaatgctt | cttccagcga | ctgatccggc | aggccgtgca | tcagatcgag attaaagcta | 780 |
| cgtagcccca | gaccg       |            |            |                      | 795 |

<210> SEQ ID NO 4
<211> LENGTH: 5796
<212> TYPE: DNA
<213> ORGANISM: Artificial Sequence
<220> FEATURE:
<223> OTHER INFORMATION: Plasmid pYG4 sequence of ansB knockout vector

<400> SEQUENCE: 4

| | | | | |
|---|---|---|---|---|
| gccccgtggc | cggggggactg | ttgggcgcca | tctccttgct | gcctcgcgcg tttcggtgat | 60 |
| gacggtgaaa | acctctgaca | catgcagctc | ccggagacgg | tcacagcttg tctgtaagcg | 120 |
| gatgccggga | gcagacaagc | ccgtcagggc | gcgtcagcgg | tgttggcgg gtgtcggggc | 180 |
| gcagccatga | cccagtcacg | tagcgatagc | ggagtgtata | ctggcttaac tatgcggcat | 240 |
| cagagcagat | tgtactgaga | gtgcacccaa | ctgatcttca | gcatcttttta ctttcaccag | 300 |
| cgtttctggg | tgagcaaaaa | caggaaggca | aaatgccgca | aaaaagggaa taagggcgac | 360 |
| acggaaatgt | tgaatactca | tactcttcct | ttttcaatat | tattgaagca tttatcaggg | 420 |
| ttattgtctc | atgagcggat | acatatttga | atgtatttag | aaaaataaac aaataggggt | 480 |
| tccgcgcaca | tttccccgaa | aagtgccacc | tgcagatctc | cgcggcatat gactagtgcg | 540 |
| gccgcgttgt | gtctcaaaat | ctctgatgtt | acattgcaca | agataaaaat atatcatcat | 600 |
| gaacaataaa | actgtctgct | tacataaaca | gtaatacaag | gggtgttatg agccatattc | 660 |
| aacgggaaac | gtcttgctcg | aggccgcgat | taaattccaa | catggatgct gatttatatg | 720 |
| ggtataaatg | ggctcgcgat | aatgtcgggc | aatcaggtgc | gacaatctat cgattgtatg | 780 |
| ggaagcccga | tgcgccagag | ttgtttctga | aacatggcaa | aggtagcgtt gccaatgatg | 840 |
| ttacagatga | gatggtcaga | ctaaactggc | tgacggaatt | tatgcctctt ccgaccatca | 900 |

-continued

```
agcattttat ccgtactcct gatgatgcat ggttactcac cactgcgatc cccgggaaaa    960
cagcattcca ggtattagaa gaatatcctg attcaggtga aaatattgtt gatgcgctgg   1020
cagtgttcct gcgccggttg cattcgattc ctgtttgtaa ttgtcctttt aacagcgatc   1080
gcgtatttcg tctcgctcag gcgcaatcac gaatgaataa caatttggtt gatgcgagtg   1140
attttgatga cgagcgtaat ggctggcctg ttgaacaagt ctggaaagaa atgcataagc   1200
tgcttttgcc attctcaccg gattcagtcg tcactcatgg tgatttctca cttgataacc   1260 ttattttga cgaggggaaa ttaataggtt gtattgatgt tggacgagtc ggaatcgcag   1320
accgatacca ggatcttgcc atcctatgga actgcctcgg tgagttttct ccttcattac   1380
agaaacggct ttttcaaaaa tatggtattg atggtcctga tatgaataaa ttgcagtttc   1440
atttgatgct cgatgagttt ttctaatcag aattggttaa ttggttgtaa cactggcaga   1500
gcattacgct gacttgacgg gacggcggct ttgttgaata aatcgaactt tgctgagtt    1560 gaaggatcag atcacgcatc ttcccgacaa cgcagaccgt tccgtggcaa agcaaaagtt   1620
caaaatcacc aactggtcca cctacaacaa agctctcatc aaccgtggct ccctcacttt   1680
ctggctggat gatggggcga ttcaggcctg gtatgagtca gcaacacctt cttcacgagg   1740
cagacctcag cgcgagctcg gccgcctagg ccgggccctc tagagaattc ttaattaacc   1800
cacgtgttga aaataaaag aaaatgccaa tgaagtatcg gcattttctt tttgctgtta    1860
ttagttgact gtcagctgtc cttgctccag gatgctgttt ttgacaacgg atgtttatt    1920 gcctttgatg ttcattaaga agctcggggc aaatgttgcc tttttatcct cgaagaagcc   1980
tctgtttgtc atgtagcttg tgataaccac attgttgcct ttggcttgcg gcactgcgaa   2040
gtgagagtaa gtgaatgtca catcgtttgg atcaagaccc atttgcagca caagccctgt   2100
tttgttcagc ggcttgtaag ggccggttaa agagtttgat acataaccaa gcatgtaaat   2160 atcgttgag ttaataccat cgatcgtcat ttttgaaccg cgtgaatcag tgaacaagta    2220
ccatttgccg ttcattttga aaacattcgc gcgctcgatt tcatcagtta ccgtgtttga   2280
agtgatcagc ggcttcatta ctttttttcaa tgtgtaatca ttattaactc tatgataccg   2340
agggcgccgt tcgctaactc agcatcgcgt ttttagcgc tctgctggag cttctggctt    2400 tcttttacgga agaagttcgt gccgccgccg tagtacgctt tgttaaataa agattcttcg   2460
ccttggtatc cgttttctgt tcccgtgttg gcttcgaata caagatattt atggcctttg   2520
tcttcaacgt agtgagggtc tctcagcgta tggttgtcgc cggatgtata attgccttca   2580
tcgataaact gctgaacgtt ctgatatgtt tttccgtctc cgtcaaaaat cgttttgtga   2640
tcttccactc cgttgatttt gagtgtgtca tcagattttg acacatttac ctgcgctgtt   2700
gtcaggcttt gtttgccgta atgtttaccg gaatagtcag tgtagaataa acggattttt   2760
ccgtcagatg taaaggttgc agaaccggac cattcttgcg tctgatcttt caggatcgga   2820
tcgttggcgt cgaacttatc gctgtcttta aagacacggc ccgcgttttt ccagctgtcg   2880
attgagttgt cgccgacctt ttgataaaac atgtagattg atgtgtcatc agcgtctttc   2940
gggcttcccg caagagcaaa cacaacgtga tagccgttgt attcagctac tgttccgtca   3000
gcgttttgca gcggccagct gtcccacaca tcaagtcctt ttgcagactc aatatttta    3060 atcgttgatt gatcgaattg aggcacttgg tattttttcgt tttgctgctg tttagggatc   3120
tgcagcatat catggcgtgt aatatgagag acgccgtacg tttctttgta tgcttttttgg  3180 ttattttctt tcgcgaaggc ttgagtcgct cctcctgcca gaagtgcagt cgtaaaagtc   3240
```

-continued

```
agaactgtgg cttgttttac aatttttttg atgttcatgt tcatgtctcc ttctgtatgt    3300 actgttttt  gcgatctgcc gtttcgatcc tcccgaattg actagtgggt aggcctaatt    3360
gcggcctagg gataacaggg taatgcggcc gcggccggcc gtcgacaagc ttggatccgc    3420
ccgggcctaa ttggccggcg cgccaaaaat ttattagagc aatatagtcc tagaatgtca    3480
aaggtaccga tcatgatcta gaattcccat gtcagccgtt aagtgttcct gtgtcactca    3540
aaattgcttt gagaggctct aagggcttct cagtgcgtta catccctggc ttgttgtcca    3600
caaccgttaa accttaaaag ctttaaaagc cttatatatt cttttttttc ttataaaact    3660
taaaacctta gaggctattt aagttgctga tttatattaa ttttattgtt caaacatgag    3720
agcttagtac gtgaaacatg agagcttagt acgttagcca tgagagctta gtacgttagc    3780
catgagggtt tagttcgtta acatgagag cttagtacgt taaacatgag agcttagtac    3840
gtgaaacatg agagcttagt acgtactatc aacaggttga actgctgatc ttcagatcct    3900
ctacgccgga cgcatcgtgg ccggatccag ccgaccaggc tttccacgcc cgcgtgccgc    3960
tccatgtcgt tcgcgcggtt ctcggaaacg cgctgccgcg tttcgtgatt gtcacgctca    4020
agcccgtagt cccgttcgag cgtcgcgcag aggtcagcga gggcgcggta ggcccgatac    4080
ggctcatgga tggtgtttcg ggtcgggtga atcttgttga tggcgatatg gatgtgcagg    4140
ttgtcggtgt cgtgatgcac ggcactgacg cgctgatgct cggcgaagcc aagcccagcg    4200
cagatgcggt cctcaatcgc gcgcaacgtc tccgcgtcgg gcttctctcc cgcgcggaag    4260
ctaaccagca ggtgataggt cttgtcggcc tcggaacggg tgttgccgtg ctgggtcgcc    4320
atcacctcgg ccatgacagc gggcaggtg tttgcctcgc agttcgtgac gcgcacgtga    4380
cccaggcgct cggtcttgcc ttgctcgtcg gtgatgtact tcaccagctc gcgaagtcg    4440 ctcttcttga tggagcgcat ggggacgtgc ttggcaatca cgcgcacccc ccggccgttt    4500
tagcggctaa aaaagtcatg gctctgccct cgggcggacc acgcccatca tgaccttgcc    4560 aagtcgtcc tgcttctctt cgatcttcgc cagcagggcg aggatcgtgg catcaccgaa    4620
ccgcgccgtg cgcgggtcgt cggtgagcca gagtttcagc aggccgccca ggcggcccag    4680
gtcgccattg atgcgggcca gctcgcggac gtgctcatag tccacgacgc ccgtgatttt    4740
atagccctgg ccgacggcca gcaggtaggc cgacaggctc atgccggccg ccgccgcctt    4800
ttcctcaatc gctcttcgtt cgtctggaag gcagtacacc ttgataggtg ggctgccctt    4860
cctggttggc ttggtttcat cagccatccg cttgccctca tctgttacgc cggcggtagc    4920
cggccagcct cgcagagcag gattcccgtt gagcaccgcc aggtgcgaat aagggacagt    4980
gaagaaggaa caccgctcg cgggtgggcc tacttcacct atcctgcccg gctgacgccg    5040
ttggatacac caaggaaagt ctacacgaac cctttggcaa aatcctgtat atcgtgcgaa    5100
aaaggatgga tataccgaaa aaatcgctat aatgaccccg aagcagggtt atgcagcgga    5160
aaagcgctgc ttccctgctg ttttgtggaa tatctaccga ctggaaacag gcaaatgcag    5220
gaaattactg aactgagggg acaggcgaga gacgatgcca aagagctaca ccgacgagct    5280
ggccgagtgg gttgaatccc gcgcggccaa gaagcgccgg cgtgatgagg ctgcggttgc    5340
gttcctggcg gtgagggcgg atgtcgaggc ggcgttagcg tccggctatg cgctcgtcac    5400
catttgggag cacatgcggg aaacggggaa ggtcaagttc tcctacgaga cgttccgctc    5460
gcacgccagg cggcacatca aggccaagcc cgccgatgtg cccgcaccgc aggccaaggc    5520
tgcggaaccc gcgccggcac ccaagacgcc ggagccacgg cggccgaagc agggggggcaa    5580 ggctgaaaag ccggccccg ctgcggcccc gaccggcttc accttcaacc caacaccgga    5640
```

```
caaaaaggat cctctacgcc ggacgcatcg tggccggcat caccggcgcc acaggtgcgg      5700
ttgctggcgc ctatctcgcc gacatcaccg atggggaaga tcgggctcgc cacttcgggc      5760
tcatgagcgc ttgtttcggc gtgggtatgg tggcag                                5796
```

<210> SEQ ID NO 5
<211> LENGTH: 568
<212> TYPE: DNA
<213> ORGANISM: Artificial Sequence
<220> FEATURE:
<223> OTHER INFORMATION: Amplified fragment of ansB knockout strains

<400> SEQUENCE: 5

```
cgctggaaaa cgatcgtaaa acgctggtta gcacgctgaa ataatttca cctcttttta       60 acggcacaga acattctgt gccgtttat tttgtatctt tctgtttttt tgatatccat       120
ctctaagaat ggcaatttga tggagatata aatctggtta attggaactc gtcacattat      180
tcatctgtaa gatagacata atgctgcaaa ttcaagtaac tggagaaata actcgatgca      240
ggtggctgcg cttatcgccc taaccctgta ggcctgataa gcgcagcgcc atcaggcaat      300
ttgccggatg gcggctcaag gtcttatccg gcctacatcg ttaccgtatt actccgccag      360
aaacagctcc agcagcgaat tcaaaaacag cttaccgtgt gggtaatct gccagtattc       420 atcgcattca ctcaggtaac cctgggcgat agctgcatca atctgtcgac gaataacgtc      480
ttcggcaagc ccggtgtatt gcgtgaattc tgcacgcggc gcggcctcca gtaaccggaa      540
acgattcata aagaactcga acggcttg                                         568
```

<210> SEQ ID NO 6
<211> LENGTH: 47
<212> TYPE: DNA
<213> ORGANISM: Artificial Sequence
<220> FEATURE:
<223> OTHER INFORMATION: ansB-up-F primer

<400> SEQUENCE: 6

```
aaaagtgcca cctgcagatc tttcgatatt tggtgggact aagtagc                    47
```

<210> SEQ ID NO 7
<211> LENGTH: 41
<212> TYPE: DNA
<213> ORGANISM: Artificial Sequence
<220> FEATURE:
<223> OTHER INFORMATION: ansB-up-R primer

<400> SEQUENCE: 7

```
gccacctgca tcgagttatt tctccagtta cttgaatttg c                          41
```

<210> SEQ ID NO 8
<211> LENGTH: 24
<212> TYPE: DNA
<213> ORGANISM: Artificial Sequence
<220> FEATURE:
<223> OTHER INFORMATION: ansB-down-F primer

<400> SEQUENCE: 8

```
aataactcga tgcaggtggc tgcg                                             24
```

<210> SEQ ID NO 9
<211> LENGTH: 40
<212> TYPE: DNA
<213> ORGANISM: Artificial Sequence
<220> FEATURE:

```
<223> OTHER INFORMATION: ansB-down-R primer

<400> SEQUENCE: 9
agtcatatgc cgcggagatc tcggtctggg gctacgtagc                40

<210> SEQ ID NO 10
<211> LENGTH: 22
<212> TYPE: DNA
<213> ORGANISM: Artificial Sequence
<220> FEATURE:
<223> OTHER INFORMATION: ansB-QJ-F primer

<400> SEQUENCE: 10
cgctggaaaa cgatcgtaaa ac                                   22

<210> SEQ ID NO 11
<211> LENGTH: 22
<212> TYPE: DNA
<213> ORGANISM: Artificial Sequence
<220> FEATURE:
<223> OTHER INFORMATION: ansB-QJ-R primer

<400> SEQUENCE: 11
caagccgttc gagttcttta tg                                   22
```

GENE ANSB KNOCKOUT MUTANT OF CITROBACTER WERKMANII AND APPLICATION THEREOF

CROSS REFERENCE TO THE RELATED APPLICATIONS

This application is based upon and claims priority to Chinese Patent Application No.: 202111141159.1, filed on Sep. 28, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBKY073_Sequence Listing.txt, created on Mar. 1, 2022, and is 14,359 bytes in size.

TECHNICAL FIELD

The present invention belongs to the field of genetic engineering, and more particularly relates to a gene ansB knockout mutant of *Citrobacter werkmanii* and an application thereof.

BACKGROUND

Bacteria of *Citrobacter* sp., as chemoorganotrophic bacteria, can grow by taking citrate as the sole carbon source, hence its name. The bacteria of this genus are all gram-negative bacteria and usually peritrichous and facultative anaerobic, have two types of metabolism, i.e., respiration and fermentation, and produce acid and gas when fermenting glucose. The bacteria of this genus are commonly found in feces of humans and animals as normal intestinal resident bacteria, are also found in soil, water, sewage and food, but are often used as conditioned pathogens isolated from clinical samples. In recent years, the bacteria of this genus have been widely applied in the fields of heavy metal ion adsorption, sewage treatment and other polluted environment treatment. The typical representative of this genus is *Citrobacter werkmanii* with typical characteristics of the *Citrobacter*. In addition, as the determination of the whole genome of the bacteria of this genus was completed and based on the advancement of genetic engineering technologies, it has become practical means to make necessary intervention and modification on the *C. werkmanii* from a genetic level to make it have a better phenotype, such as knock out a gene ompA therein to make it have a better biofilm formation capacity and better resistance to fungicides (Patent: method for improving biofilm formation of *Citrobacter werkmanii*).

ansB is a gene encoding glutaminase/asparaginase II and mainly functions to catalyze the hydrolysis of L-asparagine into aspartic acid and ammonia. The transcription of this gene is positively regulated by the cAMP receptor (CRP) and FNR proteins. Studies have shown that ansB is monocistronic, that is, this gene encodes only one protein, and the expression of this gene depends on $\sigma^{54}$. In addition, it was reported that in *Salmonella typhimurium*, ansB is necessary to inhibit T cell proliferation and cytokine production and down-regulate T cell receptor expression; and the mechanisms of ansB used to treat acute Lymphoblastic leukemia may involve in amino acid starvation of leukemia cells. Moreover, this gene also has certain effects on the colonization of human pathogens such as *Campylobacter jejuni*, *Helicobacter pylori* and *Salmonella typhimurium* in a host. However, the gene ansB in the *C. werkmanii* is 1047 bp in overall length and a protein encoded thereby has 348 amino acid sequences. Thus, this gene may have important functions in the *C. werkmanii* and may be developed by genetic engineering and other means.

However, most bacteria in nature do not exist as single cells (individuals), but aggregate with one another, and live and grow in a form of a biofilm. The biofilm, as a bacterium aggregation group, has a structure mainly including water, bacteria, extracellular polymeric substances, proteins and genetic materials, such as eDNA and RNA, and has a better phenotype than individuals, such as increased resistance to external nutritional and environmental stress. More importantly, the biofilm has a three-dimensional structure, many pores and a specific surface area, a better adsorption capacity as well as self-repair and replantation capabilities, and thus has become an important material and vector applied in the fields of environment pollution control and protein synthesis micro-factories. However, the above applications must be based on the fact that the bacteria can form enough biofilms. How to improve the biofilm formation has always been a difficult and hot spot in scientific research. In addition, the formation of biofilms is also affected and restricted by external nutrients and environmental conditions and thus we should pay more attention to the finding of the best conditions for the biofilm formation.

SUMMARY

An object of the present invention is, regarding the defect in the prior art of a relatively limited biofilm formation capacity of *C. werkmanii*, to provide a gene ansB knockout mutant of *C. werkmanii*, which improves a biofilm formation capacity of the *C. werkmanii*, thereby enhancing the application potential of the *C. werkmanii* in environment control, protein synthesis micro-factories and other aspects.

A first object of the present invention is to provide a gene ansB knockout mutant of *C. werkmanii*, which is *C. werkmanii* with a gene ansB knocked out, wherein a nucleotide sequence of the gene ansB is as shown in SEQ ID NO: 1.

The gene ansB knockout mutant of the *C. werkmanii* is *C. werkmanii* ΔansB, which is acquired by completely knocking out coding genes of ansB in a *C. werkmanii* GDFMZ BF-8 strain from site 1 to 1047, and is deposited in Guangdong Microbial Culture Collection Center (GDMCC) on the 5th Floor, Building No. 59, No. 100, Xianlie Middle Road, Yuexiu District, Guangzhou City, Guangdong Province, 510070 under the accession No. GDMCC 61849 on Aug. 2, 2021.

A second object of the present invention is to provide a method for improving a biofilm formation capacity of *C. werkmanii*, wherein the biofilm formation capacity of the *C. werkmanii* is improved by knocking out a gene ansB of the *C. werkmanii*.

Preferably, upstream and downstream homologous fragments of the gene ansB are amplified by using PCR, ligated with a plasmid pYG4 to construct a knockout vector pYG4-ansB, and then transformed with *Escherichia coli* S17-1; the *E. coli* S17-1 carrying the knockout vector pYG4-ansB and the *C. werkmanii* are subjected to conjugational transfer to acquire a gene ansB knockout mutant of the *C. werkmanii*.

Preferably, the *C. werkmanii* is *C. werkmanii* GDFMZ BF-8.

Preferably, (1) primer sequences are as follows:

ansB-up-F: aaaagtgccacctgcagatctTTCGATAT-TTGGTGGGACTAAGTAGC (SEQ ID NO: 6);

ansB-up-R: gccacctgcatcgaGTTATTTCTCCAGT-TACTTGAATTTGC (SEQ ID NO: 7);

ansB-down-F: aataacTCGATGCAGGTGGCTGCG (SEQ ID NO: 8);

ansB-down-R: agtcatatgccgcggagatctCGGTCTGGGGC-TACGTAGC (SEQ ID NO: 9);

ansB-QJ-F: CGCTGGAAAACGATCGTAAAAC (SEQ ID NO: 10); and ansB-QJ-R: CAAGCCGTTCGAGTTCTTTATG (SEQ ID NO: 11);

(2) upstream and downstream homologous sequences of the gene ansB are acquired by amplification by taking an extracted *Citrobacter werkmanii* genome DNA as a template and taking ansB-up-F and ansB-up-R as well as ansB-down-F and ansB-down-R as primers respectively;

(3) the plasmid pYG4 is subjected to single enzyme digestion with BglII and recovered by gel cutting;

(4) the amplified upstream and downstream homologous fragments of the gene ansB are ligated with the plasmid pYG4 to construct the knockout vector pYG4-ansB and then transformed with the *E. coli* S17-1 by heat shock;

(5) the *E. coli* 517-1 carrying the knockout vector pYG4-ansB and the *C. werkmanii* are co-cultured to obtain a co-culture, the co-culture is eluted, diluted and spread on a kanamycin- and rifampicin-resistant screening LB plate, and a gene ansB recombinant acquired by one-time exchange is identified by using knockout identification primers ansB-QJ-F and ansB-QJ-R; and (6) the recombinant acquired by one-time exchange is then subjected to amplification culture in an LB liquid medium, diluted and spread on an LB plate containing 5% sucrose by mass fraction, and a single clone is picked and identified with the knockout identification primers ansB-QJ-F and ansB-QJ-R to acquire the gene ansB knockout mutant of the *C. werkmanii*.

Preferably, the *C. werkmanii* is *C. werkmanii* GDFMZ BF-8.

A third object of the present invention is to provide an application of a gene ansB knockout mutant of *C. werkmanii* in heavy metal ion adsorption or protein synthesis micron factories.

Preferably, the application refers to an application under the conditions of a polypropylene attachment material, an LB medium, 30° C., and static culture.

In the present invention, the acquired engineering bacteria with the *C. werkmanii* gene ansB knocked out are cultured in LB, TSB, NB and other media at 25° C. and 30° C., so that the biofilm formation capacity of the *C. werkmanii* on a polypropylene material is improved. Thus, the application scenarios and scopes of the *C. werkmanii* in heavy metal ion adsorption and construction of cellular protein synthesis micro-factories are broadened.

A wild type strain of *C. werkmanii* GDFMZ BF-8 of the *C. werkmanii* was deposited in Guangdong Microbial Culture Collection Center (GDMCC) at 5th Floor, Building No. 59, No. 100, Xianlie Middle Road, Yuexiu District, Guangzhou City, Guangdong Province, 510070 under the accession No. GDMCC 61858 on Aug. 10, 2021.

The *C. werkmanii* ΔansB was deposited in Guangdong Microbial Culture Collection Center (GDMCC) on the 5th Floor, Building No. 59, No. 100, Xianlie Middle Road, Yuexiu District, Guangzhou City, Guangdong Province, 510070 under the accession No. GDMCC 61849 on Aug. 2, 2021.

DETAILED DESCRIPTION

The following embodiments are intended to further illustrate the present invention, but not to limit the present invention.

Wild *C. werkmanii* used in the following embodiments is *C. werkmanii* GDFMZ BF-8.

Embodiment 1

I. Construction of ansB Knockout Vector

Figure 1:
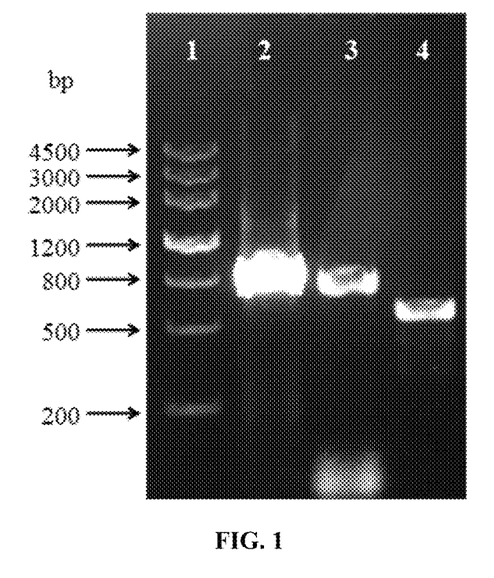
FIG. 1 is a PCR identification diagram of an ansB knockout strain ΔansB of *C. werkmanii* (lane 1: Marker III purchased from Tiangen Biochemical Technology (Beijing) Co., Ltd.; lane 2: an upstream fragment of ansB; lane 3: a downstream fragment of ansB; and lane 4: knockout identified fragment)

An upstream homologous sequence (978 bp; its nucleotide sequence was as shown in SEQ ID NO: 2), a downstream sequence (795 bp; its nucleotide sequence was as shown in SEQ NO: 3) and a plasmid pYG4 sequence (5796 bp; its nucleotide sequence was as shown in SEQ ID NO: 4) of a gene ansB (1047 bp; its nucleotide sequence was as shown in SEQ ID NO: 1 and specifically was: ATG-GAGTTTTT-CAAGAAAACGGCACTTGCCGCACTGGT-TATGGGTTTCAGCGGCGCG
GCGCTTGCACTGCCAAACATCACTATTT-TAGCAACCGGCGGGACCATTGCCGGCGGT GGT-GATTCCGCGACAAAATCTAACTA-CACGGCAGGCAAGGTAGGCGTAGAGAATCT GGTTGAAGCCGTACCTCAGTTGAAAGA-CATCGCGGTTGTTAAAGGCGAGCAGGTGG TGAA-CATCGGCTCTCAGGATATGAATGACGACGTCTGGT-TAACGCTGGCGAAAAAG
ATTAACACCGAGTGTGA-TAAAACCGACGGTTTTGTCGTGACACATGGTACG-GATACC ATGGAAGAAACTGCCTAT-TTCCTCGACCTGACCGTCAAGTGCAACAAGC CGGTAGT GCTGGTGGGTGCAATGCGTCCGTCTA-CAGGGATGAGCGCCGATGGCCCGTTCAACCT GTATAACGCAGTGGTGACGGCTGCA-GACAAAGCCTCTGCCAACCGTGGCGTGCTGG TGGTGATGAACGACACCGTGATG-
GATGGTCGCGACGTGACCAAAACCAACACTACC
GATGTAGCCACCTTCAAATCCGTTAAC-
TATGGCCCGCTGGGCTACATCCATAACGGC AAGAT-
TGACTACCAGCGTACGCCTGCGCGTAAGCACAC-
CACGTCTACTCCGTTCGAT
GTGTCTAAGCTGACCGAACTGCCGAAAGTGGG-
GATTGTTTACAACTACGCTAACGCC TCG-
GATCTGCCAGCCAAAGCGCTGGTCGACGCGGGT-
TATGCGGGTATCGTCAGTGC
GGGTGTAGGTAACGGCAACTTGTATAAAACGGTAT-
TCGATACGCTGGCCACTGCCG CGCAT-
AAAGGTACCGTCGTGGTGCGTTCCTCCCGTGTAC-
CAACCGGCTCCACCACGC
AGGATGCTGAAGTTGAT-
GATGCGAAATACGGCTTTGTGGCTTCAGGTTCTCT-
GAACC
CGCAAAAAGCGCGTGTTCTGCTGCAGCTTGCG
CTGACGCAAACCAAGGATCCTAAG CAGATCCAG-
GAAATGTTTAATCAGTATTAA) of *C. werkmanii* were copied to relevant positions of ClonExpress Multi S of software CE Design V1.04, and related settings were carried out: a vector was linearized through single enzyme digestion; the number of insert fragments was two; and BglII was selected as an enzyme digestion site for linearization. Output primer pairs ansB-up-F/ansB-up-R and ansa-down-F/ansB-down-R were designed through the software CE Design V1.04 and Guangzhou Branch of Beijing Tsingke Biotechnology Co., Ltd. was entrusted to carry out primer synthesis. Upstream and downstream homologous arms (lanes 2 and 3 in FIG. 1) of the gene ansB were respectively amplified using the primer pairs ansB-up-F/ansB-up-R and ansB-down-F/ansB-down-R and PrimeSTAR® Max DNA Polymerase (TaKaRa) by taking a genome of wild *C. werkmanii* GDFMZ BF-8 as a template.

Primer sequences were as follows:
ansB-up-F: aaaagtgccacctgcagatctTTCGATAT-
TTGGTGGGACTAAGTAGC (SEQ ID NO: 6);
ansB-up-R: gccacctgcatcgaGTTATTTCTCCAGT-
TACTTGAATTTGC (SEQ ID NO: 7);
ansB-down-F: aataacTCGATGCAGGTGGCTGCG (SEQ ID NO: 8); and
ansB-down-R: agtcatatgccgcggagatctCGGTCTGGGGC-
TACGTAGC (SEQ ID NO: 9)
Its mixed system was as follows:

| Reagent | Volume (μl) |
|---|---|
| Prime STAR Max Premix (2×) | 25 |
| Upstream primer (10 μM) | 1 |
| Downstream primer (10 μM) | 1 |
| Genome of *Citrobacter werkmanii* (100 ng/μl) | 1 |
| Sterile water | 22 |
| Total volume | 50 |

A PCR process was as follows:

| Step | Temperature | Time (s) | Cycle |
|---|---|---|---|
| 1 | 98° C. | 10 | 34 cycles were designed in total from step 1 to step 3 |
| 2 | 55° C. | 15 | |
| 3 | 72° C. | 30 | |

Products acquired by amplification through the above method were electrophoresed on a 1.0% agarose gel to confirm the correctness of the fragments and recovered corresponding upstream and downstream homologous fragments of ansB by gel cutting.

At the same time, a plasmid pYG4 was extracted with a plasmid extraction kit (Biological Engineering and Biotechnology) and enzyme digestion was carried out using the following enzyme digestion system:

| Reagent | Volume (μl) |
|---|---|
| 10 × QuickCut Buffer | 5 |
| Plasmid pYG4 (225 ng/ul) | 5 |
| BglII (1000 units/ml) | 2 |
| Sterile water | 38 |
| Total volume | 50 |

BglII used in the above enzyme digestion system was purchased from Takara Biotechnology (Beijing) Co., Ltd. and the uniformly mixed system above was put into an incubator, where it was cultured at 37° C. for 15 minutes, and digested vector fragments were recovered using a gel recovery kit (Omega).

The plasmid pYG4 vector fragments digested and recovered by gel cutting and upstream and downstream homologous arm fragments of the gene ansB were ligated according to instructions of a one-step seamless ligation kit In-Fusion® HD Cloning Kit (TaKaRa):

| Reagent | Volume (μl) |
|---|---|
| 5 × in-fusion HD enzyme premix | 2 |
| Plasmid pYG4 digested and recovered by gel cutting (42 ng/ul) | 4 |
| Upstream homologous fragment ansB-up of ansB (60 ng/ul) | 1 |
| Downstream homologous fragment ansB-down of ansB (53 ng/ul) | 1 |
| Sterile water | 2 |
| Total volume | 10 |

After uniform mixing, the above system was placed in a water bath at 50° C. for 15 minutes, and then placed on ice to terminate the reaction, and 10 μl of entire ligation reaction solution was drawn and transformed with *E. coli* S17-1 by heat shock (heat shock in a water bath at 42° C. for 90 s). The resulting product was subjected to recovery culture on a shaker for 1 h, spread on a Kana plate and placed in an incubator where it was cultured at 37° C. overnight. After a single colony grew, the single colony was picked and successfully transformed transformants were identified with primers of ansB-QJ-F and ansB-QJ-R (if the length of the amplified fragment was 568 bp, and its sequence was as shown in SEQ ID NO: 5). It was proved that the knockout vector pYG4-ansB was constructed correctly and may be used in subsequent experiments.

ansB-QJ-F: CGCTGGAAAACGATCGTAAAAC (SEQ ID NO: 10); and
ansB-QJ-R: CAAGCCGTTCGAGTTCTTTATG (SEQ ID NO: 11).

II. Conjugational Transfer and ansB Knockout Identification

The *E. coli* S17-1 carrying the knockout vector pYG4-ansB and the wild type *C. werkmanii* GDFMZ BF-8 were subjected to conjugational transfer. Specifically, the above two bacteria were respectively cultured overnight, $OD_{600}$ was regulated to be equal to 1.0 approximately, and bacterial solutions were mixed according to a volume ratio of 1:3; the mixed bacterial solution was dripped on an LB plate with a filter membrane of 0.22 μm for still standing for 2 h, and after the plate was transferred to an incubator where it was statically cultured at 37° C. for 1 d, the bacteria are eluted with PBS, appropriately diluted and spread on a double-resistant LB plate containing 100 mg/L kanamycin and 20 mg/L rifampicin for culture at 37° C. for 1-2 d. A growing colony was picked and subjected to PCR verification by using the primers ansB-QJ-F and ansB-QJ-R. A recombinant of the gene ansB acquired by one-time exchange should have two bands: a large band of 1615 bp and a small band of 568 bp.

The strains that have been successfully recombined in one exchange were subjected to amplification culture in LB liquid medium, appropriately diluted with an amplification culture bacteria solution and then streaked on an LB plate containing 5% sucrose by mass fraction. After culture for 72 h, a single colony on the plate was picked for PCR verification (lane 4 in FIG. 1) by using primers ansB-QJ-F and ansB-QJ-R to determine ansB knockout strains. The knockout strains should have been subjected to double exchange, and so only a small band may be amplified, that is, a 568-bp band (its sequence was as shown in SEQ ID NO: 5). The colony identified as positive by PCR was streaked on the LB plate containing 100 mg/L kanamycin or the LB plate containing 20 mg/L rifampicin, respectively and rifampicin-resistant and kanamycin-sensitive strains finally acted as gene ansB knockout strain of ΔansB for subsequent experiments.

The gene ansB knockout strain was designated as *C. werkmanii* ΔansB, and deposited in Guangdong Microbial Culture Collection Center (GDMCC) on the 5th Floor, Building NO, 59, No. 100, Xianlie Middle Road, Yuexiu District, Guangzhou City, Guangdong Province, 510070 under the accession No. GDMCC 61849 on Aug. 2, 2021.

III. Determination of Biofilm Formation Capacity of ansB Knockout Mutant

The biofilm formation capacity of ΔansB was determined by using three different media, i.e., a common LB medium, a nutrient broth (NB) medium and a tryptone soy broth (TSB) medium, at three temperatures (25° C., 30° C. and 37° C.). The main experimental steps were as follows: ΔansB and the wild type of *C. werkmanii* GDFMZ BF-8 were respectively cultured overnight in LB, NB and TSB, and on the second day, the concentration of each bacterial solution was adjusted to $OD_{600}=1.0$ with fresh LB, NB and TSB respectively for later use; 180 μl of fresh sterile LB medium, 180 μl of fresh sterile NB medium and 180 μl of fresh sterile TSB medium were respectively added to 96-well plates (Corning), and then 20 μl of the bacterial solution, of which the bacterial concentration was adjusted in advance was added; after the above 96-well plates, to which samples were added, were respectively placed into incubators with the temperatures of 25° C., 30° C. and 37° C. for static culture or shake culture (120 rpm) for 2 days, firstly planktonic bacteria were discarded and the 96-well plates were washed, dyeing was carried out with 0.1% crystal violet; after excess dye was eluted with sterile water, crystal violet remaining on inner well walls of the 96-well plates were eluted using 95% alcohol, light absorption values of the samples at 590 nm were determined with an enzyme-labeled instrument and were used to represent the biofilm formation. 8 repeats were set in each treatment and the treatment was repeated at least 3 times at different time.

The biofilm formation capacities of the wild type strain of *C. werkmanii* GDFMZ BF-8 and the ansB knockout mutant of ΔansB under different conditions were shown in FIGS. 2A-2F. Compared with the wild type strain of *C. werkmanii* GDFMZ BF-8, the increased multiples of the biofilm formation capacity of ΔansB under different conditions were shown in the following table.

| | | Medium | | |
| --- | --- | --- | --- | --- |
| Temperature | Culture mode | LB | NB | TSB |
| 25° | Static culture | 2.15 | 1.67 | 1.49 |
| | Shake static | 1.36 | 1.11 | 1.55 |
| 30° | Static culture | 2.68 | 1.37 | 1.73 |
| | Shake static | 1.64 | 0.93 | 0.92 |
| 37° | Static culture | 1.15 | 1.23 | 1.03 |
| | Shake static | 1.26 | 0.80 | 0.79 |

Figure 2A:
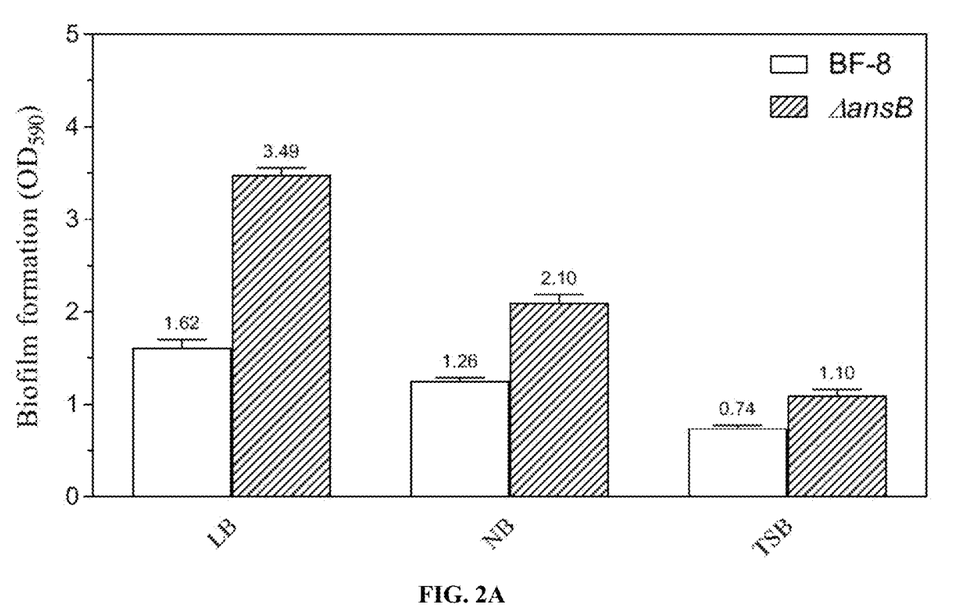
FIG. 2A shows the biofilm formation of a wild strain BF-8 of and an ansB knockout strain ΔansB of *C. werkmanii* at 25° C. and under static culture.
Figure 2B:
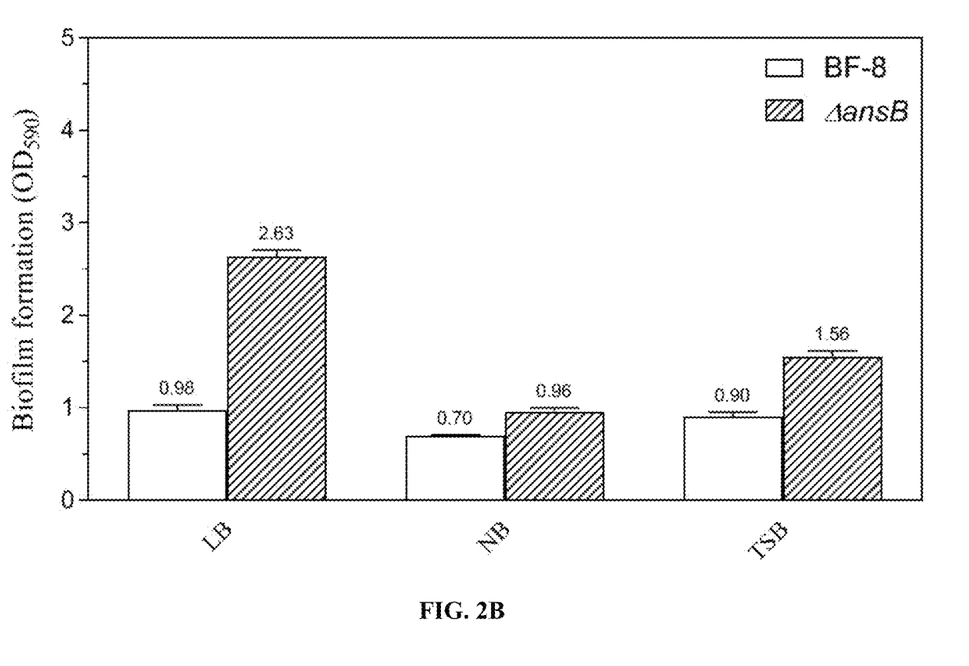
FIG. 2B shows the biofilm formation of a wild strain BF-8 of and an ansB knockout strain ΔansB of *C. werkmanii* at 30° C. and under static culture.
Figure 2C:
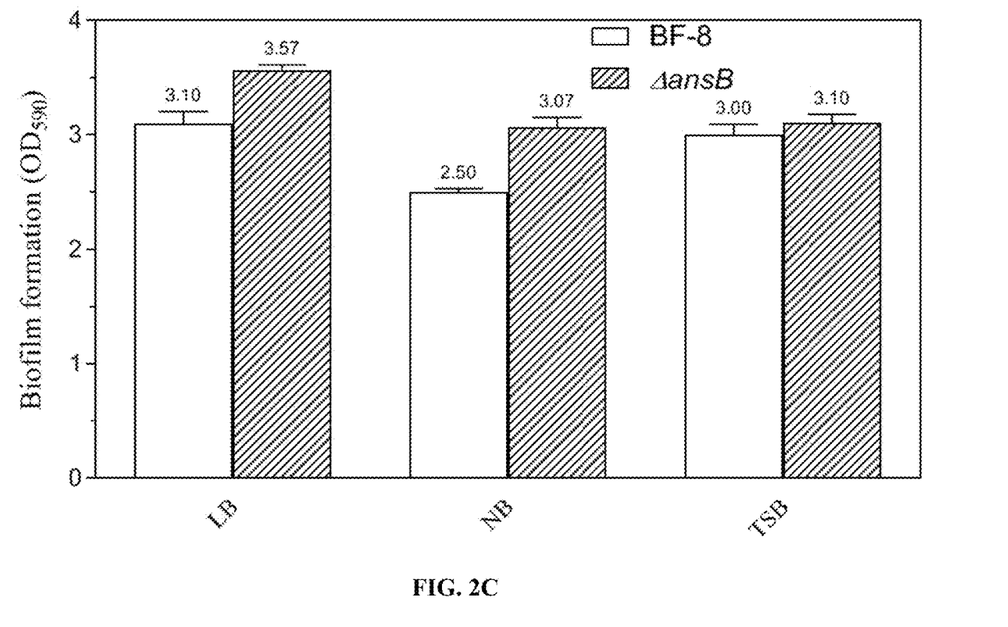
FIG. 2C shows the biofilm formation of a wild strain BF-8 of and an ansB knockout strain ΔansB of *C. werkmanii* at 37° C. and under static culture.
Figure 2D:
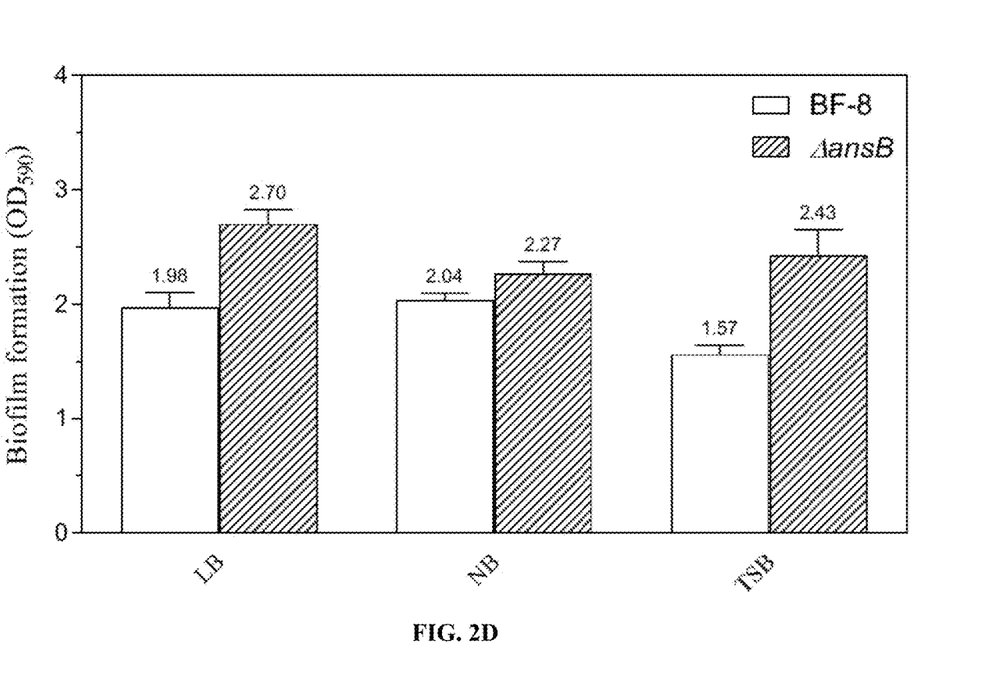
FIG. 2D shows the biofilm formation of a wild strain BF-8 of and an ansB knockout strain ΔansB of *C. werkmanii* at 25° C. and under shake culture at 120 rpm.
Figure 2E:
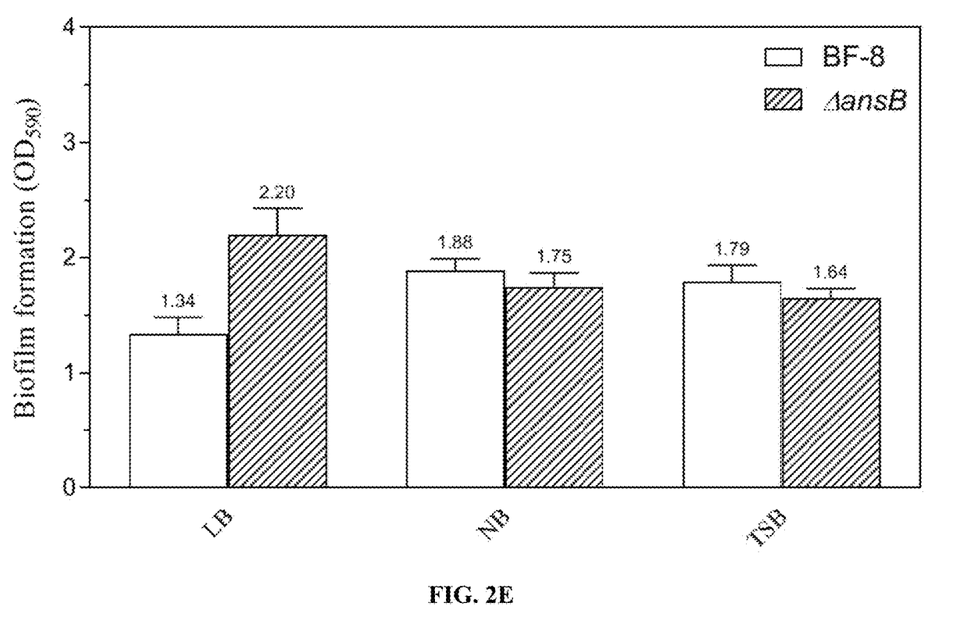
FIG. 2E shows the biofilm formation of a wild strain BF-8 of and an ansB knockout strain ΔansB of *C. werkmanii* at 30° C. and under shake culture at 120 rpm.
Figure 2F:
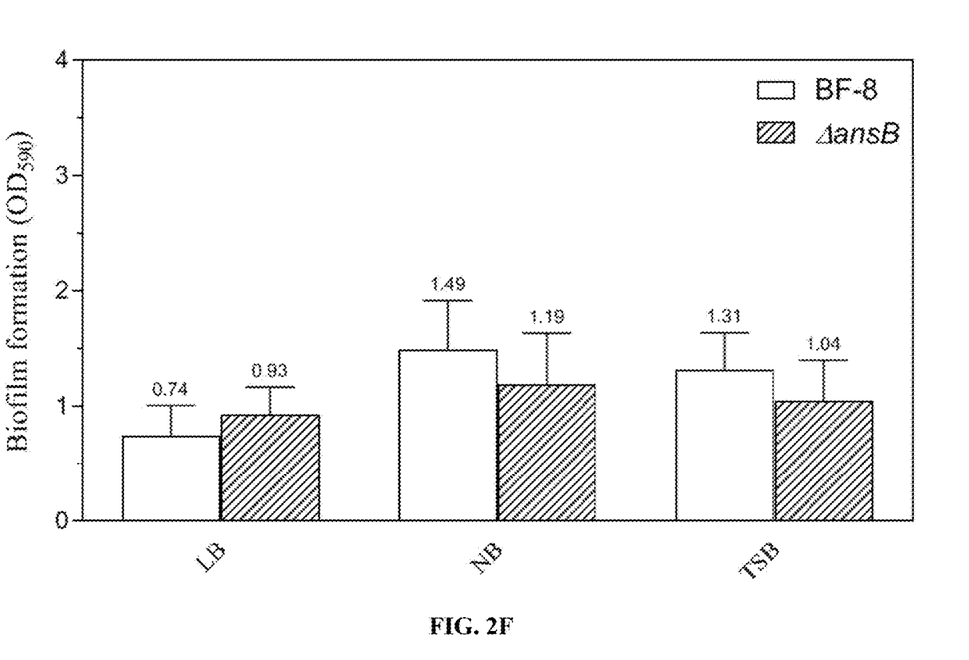
FIG. 2F shows the biofilm formation of a wild strain BF-8 of and an ansB knockout strain ΔansB of *C. werkmanii* at 37° C. and under shake culture at 120 rpm. Note: numbers above columns are average values.

It can be seen from FIGS. 2A-2F and the above table that the wild strain of *C. werkmanii* GDFMZ BF-8 may form more biofilms at a relatively high temperature (37° C.) under a static condition (FIG. 2C), but forms less biofilms at a relatively low temperature (25° C. and 30° C.) (FIGS. 2A and 2B). However, the biofilm formation capacity of ΔansB was improved in the LB medium under both static and shake cultures at 25° C., 30° C. and 37° C., was optimal at 30° C. under static culture, and improved by 2.68 times in total; was optimal at 25° C. in the NB medium under static culture (improved by 1.67 times); and was optimal at 30° C. in the TSB medium under static culture (improved by 1.73 times). In summary, ΔansB can form more biofilms than the wild strain of *C. werkmanii* GDFMZ BF-8 under the conditions of a polypropylene attachment material, the LB medium, 30° C., and static culture.

The above results showed that the biofilm formation of this strain can be improved by knocking out the gene ansB of the *Citrobacter werkmanii* (the required optimized conditions: polypropylene attachment material, LB medium, 30° C. and static culture), and the strain has practical application potential and prospects under specific conditions.

What is claimed is:

1. *C. werkmanii* ΔansB, wherein the *C. werkmanii* ΔansB has an accession No. GDMCC 61849.

2. A method for improving a biofilm formation capacity of *C. werkmanii*, wherein the biofilm formation capacity of the *C. werkmanii* is improved by knocking out a gene ansB of the *C. werkmanii*; the *C. werkmanii* is *C. werkmanii* GDFMZ BF-8 having an accession No. GDMCC 61858; and a nucleotide sequence of the gene ansB is as shown in SEQ ID NO: 1.

3. The method according to claim 2, wherein upstream and downstream homologous fragments of the gene ansB are amplified by using PCR, ligated with a plasmid pYG4 to construct a knockout vector pYG4-ansB, and then transformed with *E. coli* S17-1; the *E. coli* S17-1 carrying the knockout vector pYG4-ansB and the *C. werkmanii* are subjected to conjugational transfer to acquire a gene ansB knockout mutant of the *C. werkmanii*.

4. The method according to claim 3, wherein specific steps are as follows:

(1) primer sequences:
ansB-up-F: aaaagtgccacctgcagatctTTCGATAT-TTGGTGGGACTAAGTAGC (SEQ ID NO: 6);
ansB-up-R: gccacctgcatcgaGTTATTTCTCCAGT-TACTTGAATTTGC (SEQ ID NO: 7);
ansB-down-F: aataacTCGATGCAGGTGGCTGCG (SEQ ID NO: 8);
ansB-down-R: agtcatatgccgcggagatctCGGTCTGGGGC-TACGTAGC (SEQ ID NO: 9);
ansB-QJ-F: CGCTGGAAAACGATCGTAAAAC (SEQ ID NO: 10); and
ansB-QJ-R: CAAGCCGTTCGAGTTCTTTATG (SEQ ID NO: 11);

(2) upstream and downstream homologous sequences of the gene ansB are acquired by an amplification by taking an extracted *C. werkmanii* genome DNA as a template and taking the ansB-up-F, the ansB-up-R, the ansB-down-F, and the ansB-down-R as primers;

(3) the plasmid pYG4 is subjected to single enzyme digestion with BglII and recovered by gel cutting;

(4) the amplified upstream and downstream homologous fragments of the gene ansB are ligated with the plasmid pYG4 to construct the knockout vector pYG4-ansB, and then transformed with the *E. coli* S17-1 by heat shock;

(5) the *E. coli* S17-1 carrying the knockout vector pYG4-ansB and the *C. werkmanii* are co-cultured to obtain a co-culture, and the co-culture is eluted, diluted and spread on a kanamycin- and rifampicin-resistant screening LB plate, and a gene ansB recombinant acquired by a one-time exchange is identified by using the ansB-QJ-F and the ansB-QJ-R as knockout identification primers; and (6) the gene ansB recombinant acquired by the one-time exchange is subjected to an amplification culture in an LB liquid medium, diluted and spread on an LB plate containing 5% sucrose by mass fraction, and a single clone is picked and identified with the knockout identification primers ansB-QJ-F and ansB-QJ-R to acquire the gene ansB knockout mutant of the *C. werkmanii*.

* * * * *